United States Patent [19]

Tsukamoto et al.

[11] Patent Number: 5,374,399
[45] Date of Patent: Dec. 20, 1994

[54] SAMPLE CELL FOR IMPROVED GAS FLOW IN A GAS ANALYZER

[75] Inventors: Tokihiro Tsukamoto; Takeshi Shimada, both of Kyoto, Japan

[73] Assignee: Horiba, Ltd., Kyoto, Japan

[21] Appl. No.: 902,016

[22] Filed: Jun. 18, 1992

[30] Foreign Application Priority Data

Jun. 26, 1991 [JP] Japan ............... 3-57654[U]

[51] Int. Cl.⁵ ............................................. G01N 17/00
[52] U.S. Cl. ....................................... 422/91; 422/83; 422/102; 356/246; 356/437; 356/440; 250/343; 250/373
[58] Field of Search ............ 356/246, 437, 440; 250/343, 373; 422/102, 104, 83, 91

[56] References Cited

U.S. PATENT DOCUMENTS

| | | | |
|---|---|---|---|
| 4,177,381 | 12/1979 | McClatchie et al. | 356/440 |
| 4,301,370 | 11/1981 | Bauer | 250/435 |
| 4,374,620 | 2/1983 | Berick et al. | 356/246 |
| 4,605,855 | 8/1986 | Yamada | 250/343 |
| 4,668,091 | 5/1987 | Lagesson et al. | 356/246 |
| 4,822,166 | 4/1989 | Rossiter | 356/246 |
| 4,973,157 | 11/1990 | Krasinski et al. | 356/246 |
| 5,146,283 | 9/1992 | Parnoff et al. | 356/246 |

FOREIGN PATENT DOCUMENTS

| | | |
|---|---|---|
| 0070314 | 1/1982 | European Pat. Off. . |
| 2158220 | 11/1971 | Germany . |
| 2532777 | 7/1975 | Germany . |
| 3441280A1 | 11/1984 | Germany . |

OTHER PUBLICATIONS

John H. Perry et al. "Chemical Engineers' Handbook" Apr. 1967 pp. 5–46.

*Primary Examiner*—Donald E. Czaja
*Assistant Examiner*—Lien Tran
*Attorney, Agent, or Firm*—Price, Gess & Ubell

[57] ABSTRACT

An improved sample cell for use in a gas analyzer has a sample body with a measuring optical path extending traverse to the cell body. A sample gas inlet port is positioned at one end of the cell body, and a sample gas outlet port is positioned at the other end of the cell body. Porous plates can extend across the cell body, and appropriately-dimensioned apertures in the porous plates can ensure a consistent flow path of gas across the optical path without any stagnated flow patterns.

7 Claims, 2 Drawing Sheets

SAMPLE CELL FOR IMPROVED GAS FLOW IN A GAS ANALYZER

BACKGROUND OF THE INVENTION

1. Field of the Invention

The present invention relates to a sample cell for use in a gas analyzer capable of analyzing various kinds of components contained within a sample gas by utilizing an optical absorption characteristic of the components and, more particularly, to a sample cell construction having improved gas flow.

2. Description of Related Art

Sample cells, provided for use in a gas analyzing system, are capable of analyzing various components contained within a sample gas by radiating the gas with a beam of energy such as infrared radiation. Infrared radiation will pass through the sample cell and the sample gas contained therein from one side of the cell to the other side. An example of a sample cell has been disclosed in Japanese Patent Publication No. Sho 62-3369 and shown, for example, in FIG. 4.

Referring to FIG. 4, the sample cell 11 includes a cell body 12 having an upper gas inlet port 13 provided at one end of the cell body 12, and an upper gas outlet port 14 provided at the other end of the cell body 12. Beam transmitting windows 15a and 15b are mounted at opposite ends of the cell body. A light source 16 can be arranged opposite an entrance window 15a, while a detector 17 can be arranged opposite the exit window 15b, whereby a gas analysis can be performed on a sample gas contained within the cell body.

In operation, a sample gas is introduced into the cell body 12 through the gas inlet port 13, and will flow across the interior of the cell body to exit through the gas outlet port 14. During this process, a beam of suitable radiation is emitted from the light source 16 and is transmitted through the cell body to be incident upon the sensor or detector 17 to provide representative signals that can be analyzed to determine the components within the sample gas.

In operation, the sample gas that is introduced through the gas inlet port 13 will generally reach a steady state operation wherein the main flow of the gas will traverse the shortest distance connecting the gas inlet port 13 with the gas outlet port 14. Remote portions of the cell body 12, such as indicated by the reference letters a and b in FIG. 4, can constitute dead spaces wherein a portion of the sample gas can become stagnant and alter the uniform sampling of the gas specimen. Additionally, a problem can occur in that the displacement of the sample gas within the sample cell body 12 can be delayed and the response speed of the gas analysis can be reduced. The prior art accordingly is still seeking to optimize a sample cell for measuring components in a gas sample.

SUMMARY OF THE INVENTION

It is an object of the present invention to provide a sample cell of an improved construction for use in a gas analyzer that is capable of eliminating any uneven flow of sample gas across an optical measuring path while ensuring a uniform speedy displacement of the sample gas through the sample cell to increase the response speed of the gas analyzer.

A sample cell for use in a gas analyzer can include a cell body having an inlet port at one end and an output port at the other end, with a pair of windows positioned for defining an optical path between the respective gas ports. A porous straightening vane member, for example, a porous plate, can be used to eliminate any uneven flow of a sample gas. The porous plate is mounted traverse to the flow of the sample gas across the optical path. The strengthening vane member can be made, for example, of a plate that is punched with a plurality of small holes, a plate formed in a honeycomb structure, or a plate-like assembly comprising a plurality of metallic nets piled up tightly and fixed together. A plurality of straightening vane members may be arranged at intervals, and the number of straightening vanes can be optionally selected. The holes or ports in the plate can have a variable configuration so that the holes closest to the gas inlet port are reduced in size, while the holes furthest from the gas inlet port are increased in diameter, depending on the flow characteristics of the sample gas.

Preferably, a pair of porous plates are provided on either side of the windows that define the optical path between the respective gas inlet port and outlet port. Each of the porous plates have a plurality of openings for transmitting the sample gas in a consistent flow path across the optical path. The plurality of openings in the respective plates have progressively larger openings as they extend further away from the inlet port. The inlet port and the outlet port may be coaxial, or may be offset to extend diagonally opposite each other across the sample cell. As a result of this arrangement, the sample gas will flow in an even manner across the optical path.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved sample cell.

Figure 1:
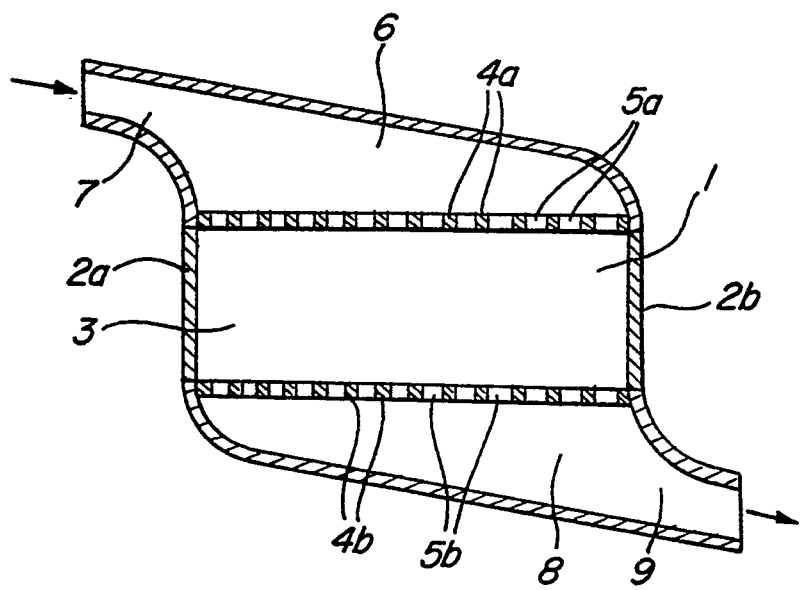
FIG. 1 is a schematic drawing showing a first preferred embodiment of the present invention.

Referring to FIG. 1, a first preferred embodiment of a sample cell for use in a gas analyzer is disclosed. The cell body 1 is provided with a pair of windows 2a and 2b having approximately the same diameter and arranged opposite each other on either side of the cell body 1 to define a measuring optical path 3. This measuring optical path 3 extends traversely across the cell body 1. A pair of straightening vane members or porous plates 4a and 4b are positioned, respectively, adjacent to and on either vertical side of the windows 2a and 2b. The porous plates 4a and 4b are positioned in a parallel arrangement, and are each provided with aperture holes 5a and 5b, respectively. These holes have a relatively small diameter and are formed across almost the entire surface of each respective plate.

A gas inlet port 7 is positioned at an upper corner of the cell body 1, and is connected to a sloping hood member 6. The hood member 6 has a curved radius portion adjacent the inlet port 7 and a curved radius portion at the outer portion adjacent the window 2b. The hood manifold 6 delivers the sample gas from the inlet port 6 in a uniform manner across the upper surface of the porous plate 4a. An outlet port 9 is positioned diagonally across the cell body 1 from the inlet port 7 and is connected to an exhaust manifold 8 having corresponding curved portions to basically form a mirror image of the inlet manifold 6.

The porous plates 4a, 4b can be formed, for example, from a metal plate that has been punched with appropriate holes or apertures in a predetermined pattern. For example, in the preferred embodiment, the holes or apertures 5a and 5b that are closest to the gas inlet port 7 are reduced in size as compared with those holes or apertures closer to the outlet port 9. These holes can further progressively increase in diameter as they extend from one side of the cell body to the other side. The diameters of the holes and their resistance to the inflowing gas can be arranged to ensure an almost equal distribution of sample gas passing traversely across the optical path defined by the windows 2a and 2b. As a result, during any measuring period when the sample gas passes through the measuring optical path 3, its flow will be almost uniformly equal between the window surfaces of 2a and 2b. Accordingly, when a measured beam is transmitted along the measuring optical path 3 through one of the windows 2a and 2b and emitted through the other of the windows 2a and 2b, a uniform measurement can be achieved. If the size of the holes is properly arranged relative to the quantity of sample gas passing through the cell body, the sample cell is capable of achieving an almost laminar flow across the optical path 3.

As can be readily appreciated, as a result of the use of these porous plates with appropriately-dimensioned holes, the quantity of the sample gas passing through the sample cell will be almost equal over the entire optical path, so that the sample gas can be more evenly and smoothly displaced. Thus, there will be no uneven or stagnant areas of sample gas in the measurement path.

As can also be appreciated, it may be possible under certain conditions to provide only one of the porous plates, depending upon certain conditions such as the flow rate of the sample gas. As an alternative embodiment, it is also possible to make the size of the gas passing holes 5a and 5b of the porous plates almost equal in diameter across their surface, again depending upon the particular flow conditions of the gas.

Finally, it is also possible to form the porous plates 4a and 4b from material that will not hinder a transmission of any optical measurement beam so that the porous plates can actually even be within the line of sight of the windows constituting the measuring optical path 3.

Figure 2:
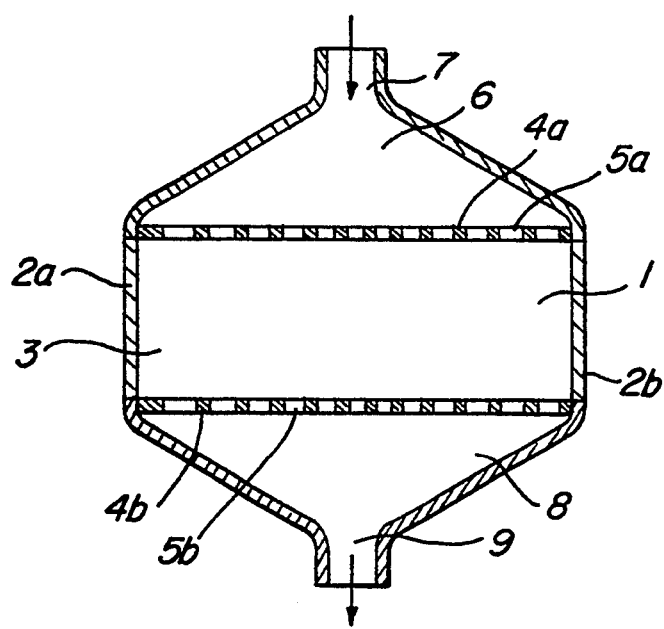
FIG. 2 is a schematic drawing showing a second preferred embodiment of the present invention.

Referring to FIG. 2, a second preferred embodiment is disclosed, wherein a gas inlet port 6 and a gas outlet port 8 are coaxially arranged with regard to the cell body 1. In a cross-sectional view, the cell body can have trapezoidal configurations representing the input and output manifolds. Thus, the input manifold 6 can have a conical configuration, and the output manifold 8 can have a conical configuration about a cylindrical center section having window ports 2a and 2b formed on opposite sides. The gas inlet port 7 is arranged on the same axis as the gas outlet port 9. A pair of porous plates 4a and 4b extend traversely across the central portion of the cell body 1 and have, respectively, gas passing apertures or holes 5a and 5b. As can be seen, the holes immediately adjacent the inlet gas port 7, on the central axis, are of a smaller dimension than the holes that are radially outward towards the edges of the respective plates. These holes can progressively increase in diameter from the center to the outer edges of those respective plates. Again, this arrangement enables the sample gas to be evenly distributed across the entire optical path 3 so that it flows through the sample cell in an even and expedient manner, as can be determined from the first and second preferred embodiments.

Figure 3:
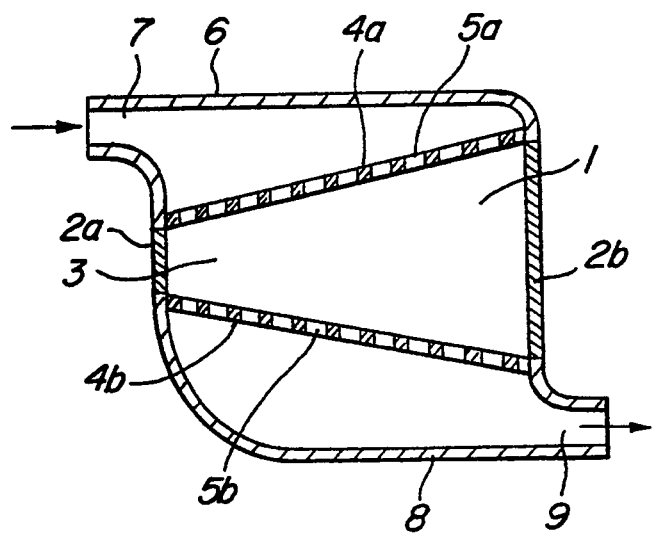
FIG. 3 is a schematic drawing showing a third preferred embodiment of the present invention.
Figure 4:
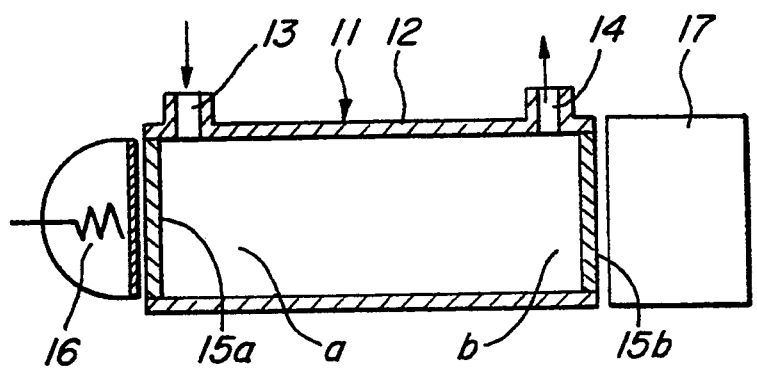
FIG. 4 is a schematic diagram showing a conventional prior art arrangement.

Referring to FIG. 3, a third preferred embodiment of the present invention is disclosed, wherein the sample cell body 1 has a window 2a of a smaller diameter than the window 2b, with the respective porous plates 4a, 4b extending from the top of each of these windows and the bottom of each of these windows in a truncated fashion across the cell body. Each of the respective porous plates 4a and 4b have a series of holes that extend at an angle to the plane of the respective porous plates, so that they maintain a perpendicular or traverse alignment to the optical axis of the optical path 3 between the respective windows. Again, the holes 4a and 4b respectively increase in diameter as they extend from the small window 2a to the larger window 2b.

A gas inlet port 7 is positioned at one corner that is diagonally opposite the gas outlet port 9 at the other corner. The upper manifold hood 6 initially delivers the gas in a path parallel to the optical axis of the windows, and then the plate 4a diverts the sample gas to extend traverse to the optical axis and through the exit porous plate 5b. The lower exhaust manifold 8 has a curvilinear configuration on one side of the exit manifold 8 relative to the exit port 9 to ensure a smooth flow of gas through the sample cell.

In this embodiment of the sample cell 1, the sample gas is introduced through the gas inlet port 7 and disbursed across the entire surface of the upper porous plate 4a so that it passes through the gas distributing holes 5a. The holes 5a are appropriately dimensioned so that the sample gas can be evenly transmitted across the measuring windows 2a and 2b. As can be appreciated, the respective sizes of the holes are determined taking into consideration the flow characteristics of the specific sample gas.

In each of the embodiments of the present invention, a cell body having an optical path through which a sample of gas can be monitored is provided, with the sample gas inlet port being provided at one end of the cell body, and a sample gas outlet port being provided at the other side of the cell body. One or more plate members can be positioned to extend approximately parallel to the optical path to create an even flow of sample gas without any stagnation across the cell body.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A sample cell for use in a gas analyzer comprising:
   a cell body having only a single inlet port at one end and an outlet port at the other end, and a pair of windows for defining an optical path between the respective ports, and
   a pair of porous plates having a plurality of openings for transmitting sample gas in a consistent flow path traversely across the optical path, the plates extending across the cell body on either side of the windows, the plurality of openings having progressively larger openings as they extend further away from the single inlet port.

2. The sample cell of claim 1 wherein the inlet port and the outlet port are coaxial with a center of the porous plates and the center portion of the porous plate openings being smaller than an outer portion of openings.

3. The sample cell of claim 1 wherein the cell body has a conical entrance manifold and a conical exit manifold.

4. The sample cell of claim 1 wherein the inlet port is positioned so that the entrance flow of sample gas is traverse to a plane in which a window lies.

5. The sample cell of claim 1 wherein the cell body has an offset entrance conical hood manifold and an offset exit conical hood manifold relative to the center portion of the porous plates.

6. The sample cell of claim 4 wherein a truncated optical path is provided and the porous plates extend away from each other from one side of the cell body to the other side of the cell body.

7. A sample cell for use in a gas analyzer comprising:
   a cell body having only a single inlet port at one end and an outlet port at the other end, the respective ports being diagonally positioned across the interior of the cell body, and a pair of windows for defining a truncated optical path between the respective ports, and
   a pair of nonparallel porous plates mounted in the cell body and having a plurality of openings for transmitting sample gas in a consistent flow path traversely across the optical path, the plates extending across the cell body on either side of the windows, the plurality of openings having progressively larger openings as they extend further away from the single inlet port and as the porous plates extend away from each other.

* * * * *